United States Patent
Franjic et al.

(10) Patent No.: US 10,945,615 B2
(45) Date of Patent: Mar. 16, 2021

(54) SUCTION TOOL WITH INTEGRATED OPTICAL PROBE AND USE THEREOF

(71) Applicant: SYNAPTIVE MEDICAL INC., Toronto (CA)

(72) Inventors: Kresimir Franjic, Toronto (CA); Luc Gilles Charron, Toronto (CA); Siu Wai Jacky Mak, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 599 days.

(21) Appl. No.: 15/573,348

(22) PCT Filed: Feb. 24, 2017

(86) PCT No.: PCT/IB2017/051096
§ 371 (c)(1),
(2) Date: Nov. 10, 2017

(87) PCT Pub. No.: WO2018/154362
PCT Pub. Date: Aug. 30, 2018

(65) Prior Publication Data
US 2018/0368703 A1 Dec. 27, 2018

(51) Int. Cl.
*A61B 5/0215* (2006.01)
*A61F 2/958* (2013.01)
(Continued)

(52) U.S. Cl.
CPC ........ *A61B 5/0215* (2013.01); *A61B 1/00165* (2013.01); *A61B 1/3137* (2013.01); *A61B 5/0035* (2013.01); *A61B 5/0055* (2013.01); *A61B 5/0066* (2013.01); *A61B 5/0084* (2013.01); *A61B 5/065* (2013.01);
(Continued)

(58) Field of Classification Search
CPC ... A61B 5/0215; A61B 5/0084; A61B 5/0066; A61B 5/065; A61B 5/0035; A61B 5/0055; A61B 5/14503; A61B 1/3137; A61B 1/00165; A61B 17/320016; A61M 1/008; A61M 25/00; A61M 2205/3313; A61F 2/958; G02B 6/0006; G02B 23/2423
See application file for complete search history.

(56) References Cited

U.S. PATENT DOCUMENTS 3,866,599 A 2/1975 Johnson
5,522,868 A * 6/1996 Buckley ............... A61B 5/0071
600/317
(Continued)

*Primary Examiner* — Peter Luong

(57) ABSTRACT

A device and method is provided for a suction tool combined with an optical probe. A suction device is provided having a tip with a hollow tubular body, a plurality of optical fibers embedded in the tip and a concentric ring attached to the tip, wherein the ring end has an inner beveled reflective surface opposing the optical fibers. A method is provided for optically measuring tissue in a medical procedure comprising suctioning a tissue using a suction device, sending optical signals along optical fibers through the suction device; directing the signals from the optical fibers onto the tissue using a beveled surface; receiving optical signals from the tissue in optical fibers via the beveled reflective surface; measuring the received optical signals in a spectrometer or detector; and releasing, resecting or ablating the tissue through the suction device.

19 Claims, 9 Drawing Sheets

(51) Int. Cl.
*A61M 25/00* (2006.01)
*A61B 5/00* (2006.01)
*A61B 5/145* (2006.01)
*F21V 8/00* (2006.01)
*G02B 23/24* (2006.01)
*A61B 1/313* (2006.01)
*A61B 1/00* (2006.01)
*A61B 5/06* (2006.01)
*A61M 1/00* (2006.01)
*A61B 17/32* (2006.01)

(52) U.S. Cl.
CPC .......... *A61B 5/14503* (2013.01); *A61F 2/958* (2013.01); *A61M 1/008* (2013.01); *A61M 25/00* (2013.01); *G02B 6/0006* (2013.01); *G02B 23/2423* (2013.01); *A61B 17/320016* (2013.01); *A61M 2205/3313* (2013.01)

(56) References Cited

U.S. PATENT DOCUMENTS

| | | | | |
|---|---|---|---|---|
| 2006/0036164 | A1* | 2/2006 | Wilson | A61B 5/06 600/424 |
| 2007/0015978 | A1* | 1/2007 | Kanayama | A61B 5/14532 600/310 |
| 2007/0270717 | A1 | 11/2007 | Tang et al. | |
| 2014/0276201 | A1* | 9/2014 | Woloszko | A61B 5/14546 600/562 |
| 2016/0058494 | A1* | 3/2016 | Vayser | A61B 90/30 600/249 |
| 2017/0014202 | A1* | 1/2017 | Ransbury | A61B 18/02 |

* cited by examiner

SUCTION TOOL WITH INTEGRATED OPTICAL PROBE AND USE THEREOF

CROSS-REFERENCES TO RELATED APPLICATIONS

This application is a national stage application of international patent application no. PCT/IB2017/051096 filed on Feb. 24, 2017, which is incorporated herein in its entirety.

FIELD

The present disclosure relates to image-guided medical procedures and more specifically to an image-guided suction tool for medical procedures.

BACKGROUND

Surgical procedures have been greatly assisted by the implementation of navigation systems. Navigation systems assist in surgery by providing previously acquired imaging information, such as magnetic resonance imaging (MRI), during surgery to visualize tissue morphology and locate target areas. Navigation systems may also be used to track surgical instruments and their location within the tissue during surgery, typically incorporating information from previously acquired imaging data.

As an example, minimally invasive brain surgery may incorporate navigation systems to map a target area for surgical resection and subsequently to access the target area with surgical tools with minimal damage to healthy brain tissue. A navigation system typically includes a tracking device or object marker on a surgical tool and a detector to detect the position of the tracking device.

By tracking a surgical tool, its insertion can be guided within the tissue with minimal impact to healthy tissue and the tool can be positioned correctly to serve its purpose. The tool may be tracked by overlaying a map of its position over a previously acquired or real-time imaging of the tissue. Likewise, other navigated procedures, such as spine, ENT (ear nose throat), orthopedic and cardiac procedures benefit from providing surgical tools with a tracking device.

A difficulty in incorporating navigation systems in surgery is that surgical procedures that exert pressure on tissues and organs or alter their composition may produce deformation of tissue. For example, deformation of brain tissue may occur when a craniotomy is opened and pressure on the brain is relieved, when a surgical device such as a surgical port or catheter is introduced into the brain, or when tissue is removed during surgery such as in a tumor resection. The tissue deformation may render the surgical plan based on pre-operative imaging inaccurate and reduce the usefulness of the image-guided therapy. Thus there is a need for real-time information on tissue structure, state, type and molecular content during surgery.

SUMMARY

An object of the present invention is to provide devices and methods for an integrated suction tool and optical probe.

Thus by one broad aspect of the present invention, a suction device for use in a medical procedure is provided, comprising an elongated tip, having a hollow tubular body, a tip proximal end and a tip distal end; a plurality of optical fibers embedded in the tip body, extending from the tip proximal end to near the tip distal end and externally accessible at the tip proximal end and near the tip distal end; and a concentric ring attached to the tip, having a first end and a second end, wherein the first end is attached to the tip distal end and the first end has an inner beveled reflective surface opposing the optical fibers near the tip distal end.

By another broad aspect of the present invention, a suction device for use in a medical procedure is provided comprising an elongated tip, having a hollow tubular body with a tip inner wall, a tip outer wall, a tip proximal end and a tip distal end; one or more channels in the tip outer wall extending from the tip proximal end to near the tip distal end; optical fibers within the channels; optical ports through the tip inner wall and extending from the channels near the tip distal end, for optical signal passage; and a concentric ring attached to the tip, having a first end and a second end, wherein the first end is attached to the tip distal end and the first end has an inner beveled reflective surface opposing the optical ports near the tip distal end;

By another broad aspect of the present invention, a method is provided for optically measuring tissue in a medical procedure, comprising: suctioning a tissue using a suction device; sending an optical signal along one or more optical fibers through the suction device; directing the optical signal from the optical fibers onto a tissue using a beveled surface; receiving optical signals from the tissue in optical fibers via the beveled reflective surface; measuring the received optical signals in a spectrometer or detector: and releasing or resecting the tissue through the suction device.

By a further broad aspect of the present invention, a method is provided for optically measuring tissue prior to ablation in a medical procedure, comprising: sending an optical signal along one or more optical fibers through a suction device: directing the optical signal from the optical fibers onto a tissue using a beveled surface; receiving optical signals from the tissue in optical fibers via the beveled reflective surface; measuring the optical signals in a spectrometer or detector; and ablating the tissue using optical signals along the optical fibers.

A further understanding of the functional and advantageous aspects of the disclosure can be realized by reference to the following detailed description and drawings.

DETAILED DESCRIPTION

Figure 1:
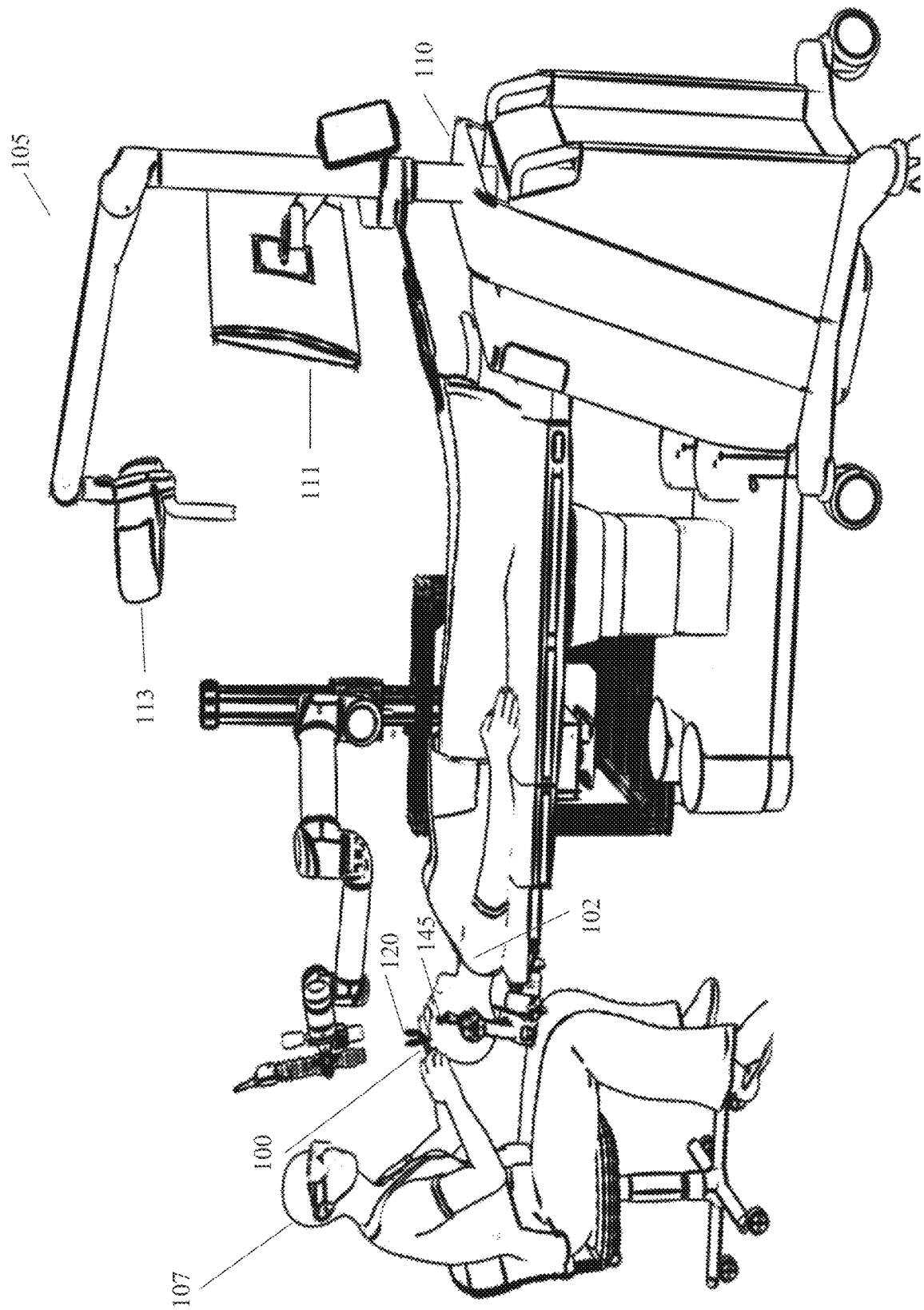
FIG. 1 depicts a non-limiting embodiment of an operating theatre.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide suction devices that are insertable into a subject or patient for manipulation of internal tissues, and methods of use thereof.

Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

Several embodiments of the present disclosure seek to address the aforementioned inadequacies of existing devices and methods to support surgical procedures utilizing surgical tools.

Minimally invasive brain surgery using access ports is a recently conceived method of performing surgery on brain tumors previously considered inoperable. One object of the present invention is to provide a system and method to assist in minimally invasive brain surgery. To address intracranial surgical concerns, specific products such as the NICO Brain-Path™ port have been developed for port-based surgery.

Surgical Navigation System

The description below makes reference to the brain as an example of tissue to which the techniques herein may be applied. It will be understood, however, that those techniques may also be applied to a wide variety of other tissues. Thus, when the brain is mentioned below, it is simply an example of the various tissues in connection with which the systems and methods herein may be implemented. In particular, suction tools are widely used in surgery, thus a suction tool combined with an optical probe will be useful in virtually all types of navigated procedures. Other examples of navigated procedures wherein a suction tool/optical probe would be useful are spine, ENT (ear nose throat), orthopedic and cardiac surgery.

FIG. 1 illustrates systems and equipment of an exemplary neurosurgical procedure. Referring to FIG. 1, an exemplary navigation system 105 which may be used in surgery is shown. A surgeon 107 conducts a surgery on a patient 102 in an operating room environment. The medical navigation system 105 is illustrated including an equipment tower 110, supporting a computing device (not shown) such as a desktop computer, as well as one or more displays 111 connected to the computing device for displaying images provided by the computing device.

Equipment tower 110 also supports a tracking system 113. Tracking system 113 is generally configured to track the positions of one or more tracking markers 120 mounted on access port 100, any of the surgical tools, or any combination thereof. Such markers, also referred to as fiducial markers, may also be mounted on patient 102, for example at various points on the head 145 of patient 102. Tracking system 113 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 113 to the computing device in equipment tower 110 for subsequent use.

Each tracked object generally includes three or more markers fixed at predefined locations on the object. The predefined locations, as well as the geometry of each tracked object, are configured within tracking system 113, and thus tracking system 113 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 113 is the "Polaris" system available from Northern Digital Inc.

The navigation system 105 may utilize reflective sphere markers in combination with a stereo camera system, to determine spatial positioning and pose of the medical instruments and other objects within the operating theater. Differentiation of the types of objects and their corresponding virtual geometric volumes may be determined by the specific orientation of the reflective spheres relative to one another giving each virtual object an individual identity within the navigation system 105. This allows the navigation system 105 to identify the medical instrument or other object and its corresponding virtual overlay representation. The location of the markers also provides other useful information to the tracking system 113, such as the object's central point, central axis, orientation, and other information related to the object. Alternatively, rather than reflective sphere markers, other navigation systems may incorporate stickers that are reflective or that have printed patterns for machine vision recognition, active tracking where either LED or RF (radio over fiber) signals are emitted to a camera or detector for tracking, or future tracking technologies that forego tracking markers altogether.

Surgical navigation systems assist in surgery by providing pre-operative imaging information, such as magnetic resonance imaging (MRI), during surgery to visualize tissue morphology, locate target areas and track surgical instruments and their location within the tissue. However, tissues may shift between the time of the pre-operative imaging and the surgery, and the surgical procedure itself produces movement and deformation of tissue. Consequently, the pre-operative images may not accurately reflect the location of the target tissue for surgery. Thus, if a surgeon guides a suction tool to a target tissue using previously acquired image data, healthy tissue may be retained by the suction tool and trauma or removal of healthy tissue may result.

The present disclosure provides tools and methods that integrate surgical tools with imaging and/or spectroscopic tools to provide real-time information such as tissue structure, state, type and molecular content intraoperatively. To obtain such information in a surgical area without disturbing the workflow of surgery, it is beneficial to integrate the optical tools into a conventional tool such as a suction device. Furthermore, to correlate the results obtained with the optical device with other imaging modalities such as MRI, PET (positron emission tomography) and CT, or the pathology results (i.e. the gold standard), it is useful to have the location tracked and recorded by a navigation system.

An important surgical tool is a suction device, which can be used for tissue retention, resection and removal of fluids. A suction device typically includes a handle portion and tip portion. The tip portion can be any one of multiple configurations, such as different lengths, angles and diameters, and may be removable so it can be swapped out to provide the most appropriate configuration for the surgical procedure. The dynamic configuration of the suction device renders the suction tip challenging to track during surgery.

Suction Tool

Figure 2:
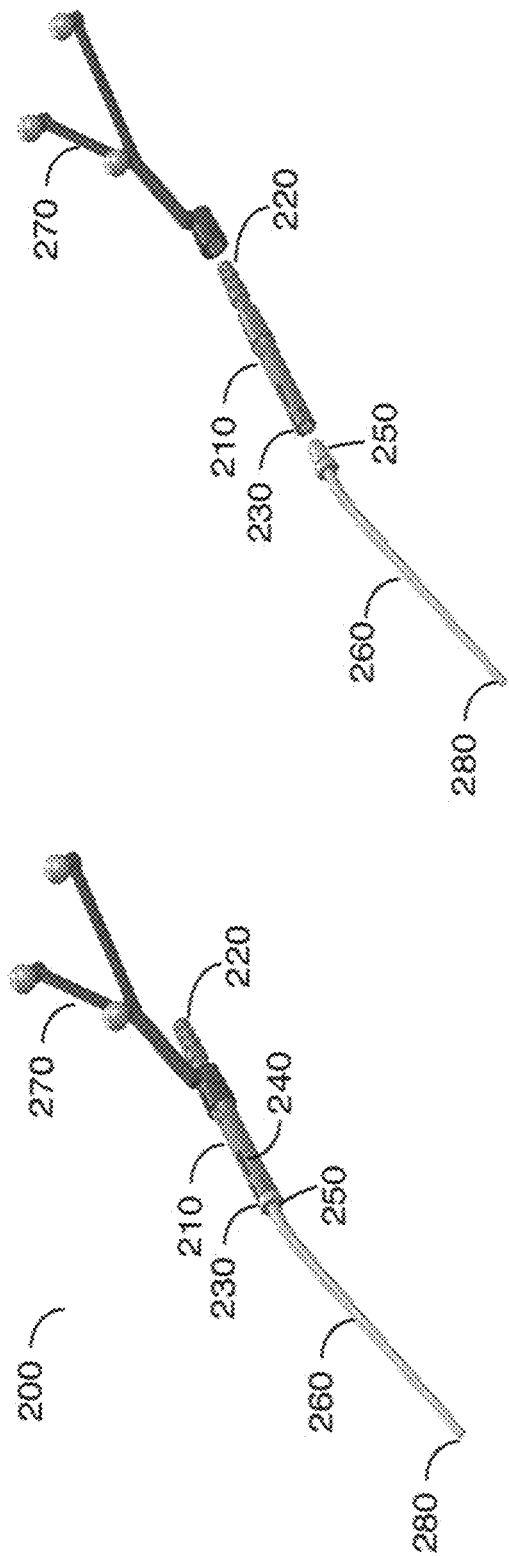
FIG. 2 illustrates an assembled and exploded view of a tracked suction device.

Referring to FIG. 2, an example of a suction tool 200 that may be tracked during surgical procedures is shown. A hollow substantially cylindrical handle 210 has a proximal end 220 and a distal end 230. The handle proximal end 220 is tapered for connection to a suction tube (not shown). The handle includes a tapered elongated slot 240 such as a tear-shaped orifice in the wall of the handle, which is widest at the proximal end and narrowest at the distal end, for controlling the amount of suction provided by the suction tool. The handle distal end 230 is connected to a proximal end 250 of a tubular hollow tip 260. The connection could be, for example, through a snap mechanism as is known in the art. The snap mechanism may include one or more outwardly protruding tabs on the tip proximal end 250 and complementary indentations on the inner surface of the hollow handle distal end 230, thus providing a key and slot method for locking connecting parts in specific rotational angles relative to the central axis. A reference tree 270 is attached to the handle 210 by sliding the reference tree over the handle proximal end 220, where it may also be engaged by a snap mechanism. The handle 210 can be used to hold and manipulate the suction tool 200, such that the tip distal end 280 is directed to the tissue, for example for holding or resecting tissue or suctioning fluids. The tip distal end 280 is also blunted to minimize trauma to tissue while in use. The reference tree 270 provides an optical marker for tracking the position of the suction tool 200 and provides the position information to the tracking system 113. The tip 260 can be removed from the handle 210 by disengaging the snap mechanism. The tip 260 may be one of several different lengths, angles and diameters. Thus, by removing and replacing the tip 260, the suction tool may have different configurations. Information on the parameters for a given tip, such as tip length, diameter and angle, can be entered and stored by the computing device of the navigation system 105, so that for each tip 260 used with the suction tool 200, the position of the tip distal end 280 is accurately tracked.

Figure 3:
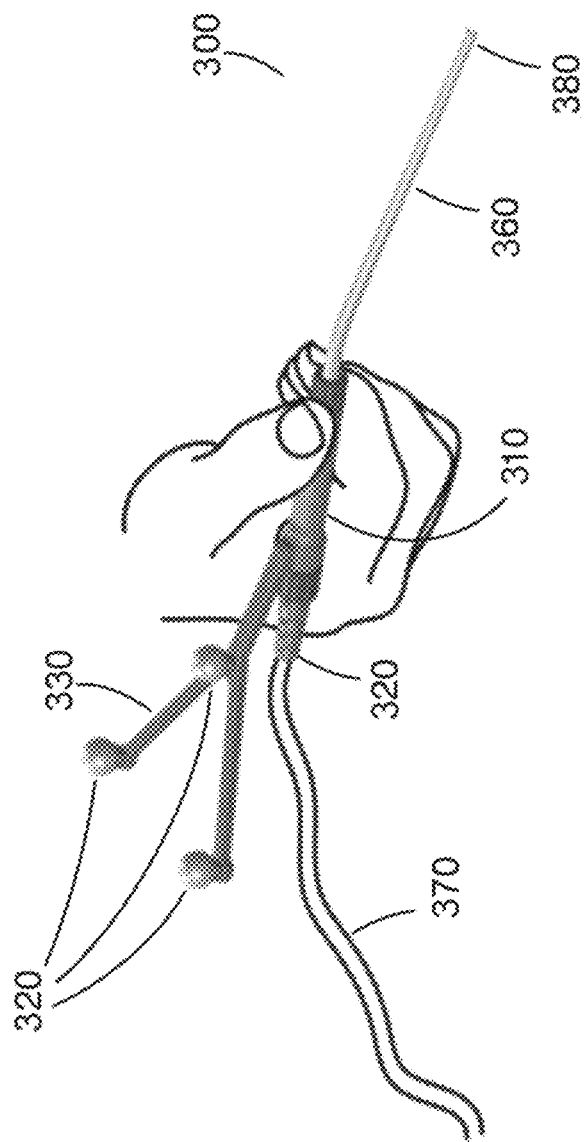
FIG. 3 illustrates a tracked suction tool held in the hand of a user.

Referring to FIG. 3, a suction tool 300 is held by user (i.e., a surgeon), with the tracking markers 320 of the reference tree 330 providing positional information of the suction tool 300 to the tracking system 113, so the navigation system 105 is able to calculate and display the position of the suction tool tip 360 to the user. Suction tool 300 is connected to suction hose 370 at the tapered proximal end 320. The tapered aspect of proximal end 320 ensures for a tight and secure fit with suction hose 370.

As seen in FIGS. 2 and 3, the suction tool (200, 300) is equipped with a bendable hollow tip (260, 360) wherein the tip includes a bend between the proximal end and distal end. The bend angle may range between 60 and 180 degrees, and preferably 70 to 170 degrees. The bend can be pre-configurable or can be further bent by the user during the medical procedure. The hollow tip may range in length between 50 mm and 250 mm in length, and preferably between 100 mm and 175 mm. Further, the hollow tip may have a diameter between 3 and 34 FR in diameter, and preferably between 5 FR and 20 FR.

Suction Tool/Optical Probe

To accommodate shifts or deformation in the tissue, assist in guiding the suction tool and provide additional information about the tissue during surgery (e.g. tissue state, content and type), a suction tool is provided that is combined with an optical probe. The suction device/optical probe provides real-time imaging or spectroscopic characterization of tissue accessed by the suction tool/optical probe. The combined device allows tissue measurements as the suction tool is inserted into the tissue and at the site of the target tissue. The optical probe of the suction tool also provides for confirmation that the target tissue is opposed to the suction tip prior to suction and that all target tissue is removed by the suction tool.

The optical probe aspect of the suction device may be used for imaging applications, for example optical coherence tomography (OCT) or other white light imaging techniques. Alternatively, the optical probe may be used for spectroscopy and fluorescence techniques, for example Raman, time resolved and spectrally resolved fluorescence.

Figure 4:
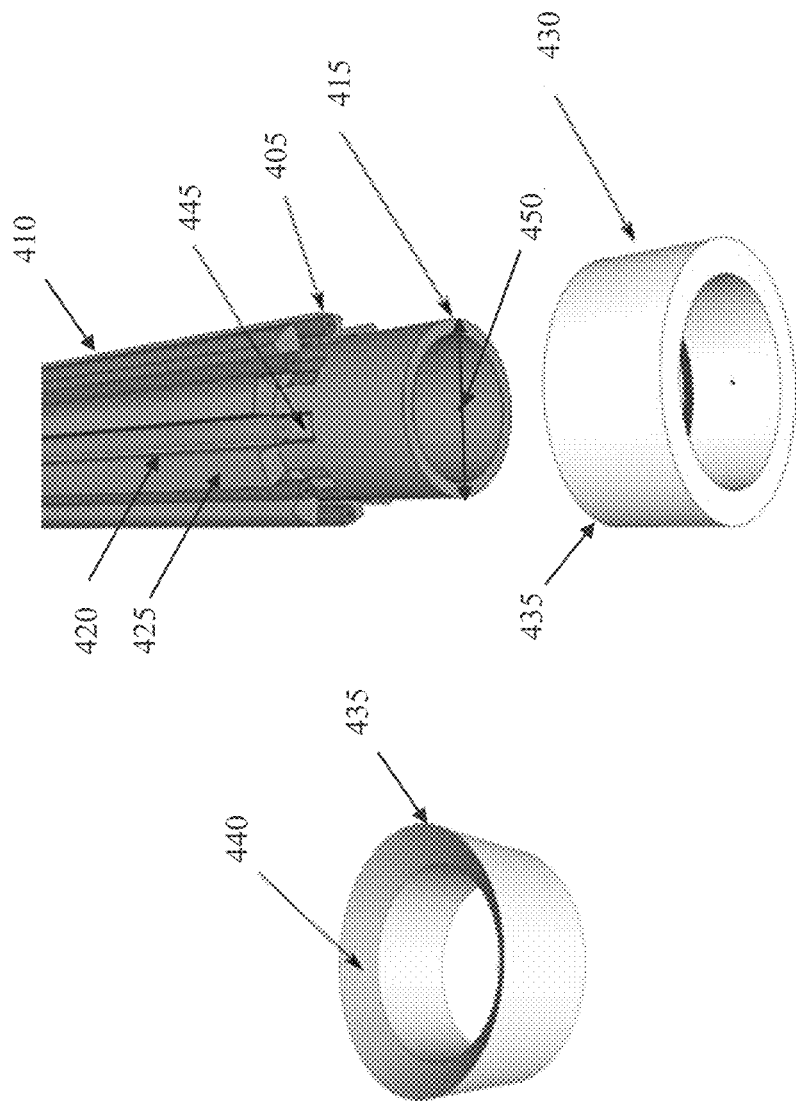
FIG. 4 illustrates an exploded view of an embodiment of a suction tool tip combined with an optical probe.

An embodiment of the combined suction/optical probe is illustrated in FIG. 4. A plurality of optical fibers 405 are embedded along the length of the suction tool tip 410 and extend close to the distal end 415 of the tip. The optical fibers 405 may be embedded in longitudinal channels 420 in the outer wall 425 of the tip 410. The optical fibers 405 may also be coated, for example metal coated, to provide strength and allow flexibility if the tip 410 is bent. A concentric ring 430 is attached to the suction tip distal end 415. A proximal end 435 of the ring is beveled inwards and has a reflective surface 440, so that when positioned on the distal end of the tip 415, the beveled surface can reflect optical signals from and to the optical fibers 405.

The ring 430 may be a molded plastic piece, such as an injection molded plastic. Possible plastic materials for the ring 430 include plolystyrene, polycarbonate, acrylic, zeonex and ultem. After molding the plastic ring 430, the beveled proximal end 435 can be coated with optical coatings that are highly-reflective for excitation and signal optical wavelengths to comprise a reflective surface 440. The reflective surface 440 may be a metal coating of the beveled proximal end 435, incorporating any common metal that is first machined and then polished by diamond turning. High resolution optical coating can also be applied to increase the performance. Examples of materials that may be used for reflective coatings are zinc sulfide, titanium dioxide, magnesium fluoride and silicon dioxide.

The angle and position of the beveled proximal end 435 may vary and can be further optimized by introducing convex and concave local areas on the beveled proximal end for focusing and defocusing the optical beams.

In this example, ports or openings 445 on the inside of the tip wall align with the ends of the optical fibers 405 and allow optical signals to pass from and to the optical fibers. The ports 445 may be sealed with an optically transparent resin. The outer diameter 450 of the tip is decreased for a length at the tip distal end 415, the smaller outer diameter overlapping with the distal end of the optical fibers 405, so that the ring 430 can slide onto the tip 410. In an alternate embodiment, the optical fibers 405 extend to the distal end of the tip 415 and the beveled proximal end 435 of the ring 430 abuts the distal end of the tip. In both examples, the ends of the optical fibers are externally accessible.

Figure 5:
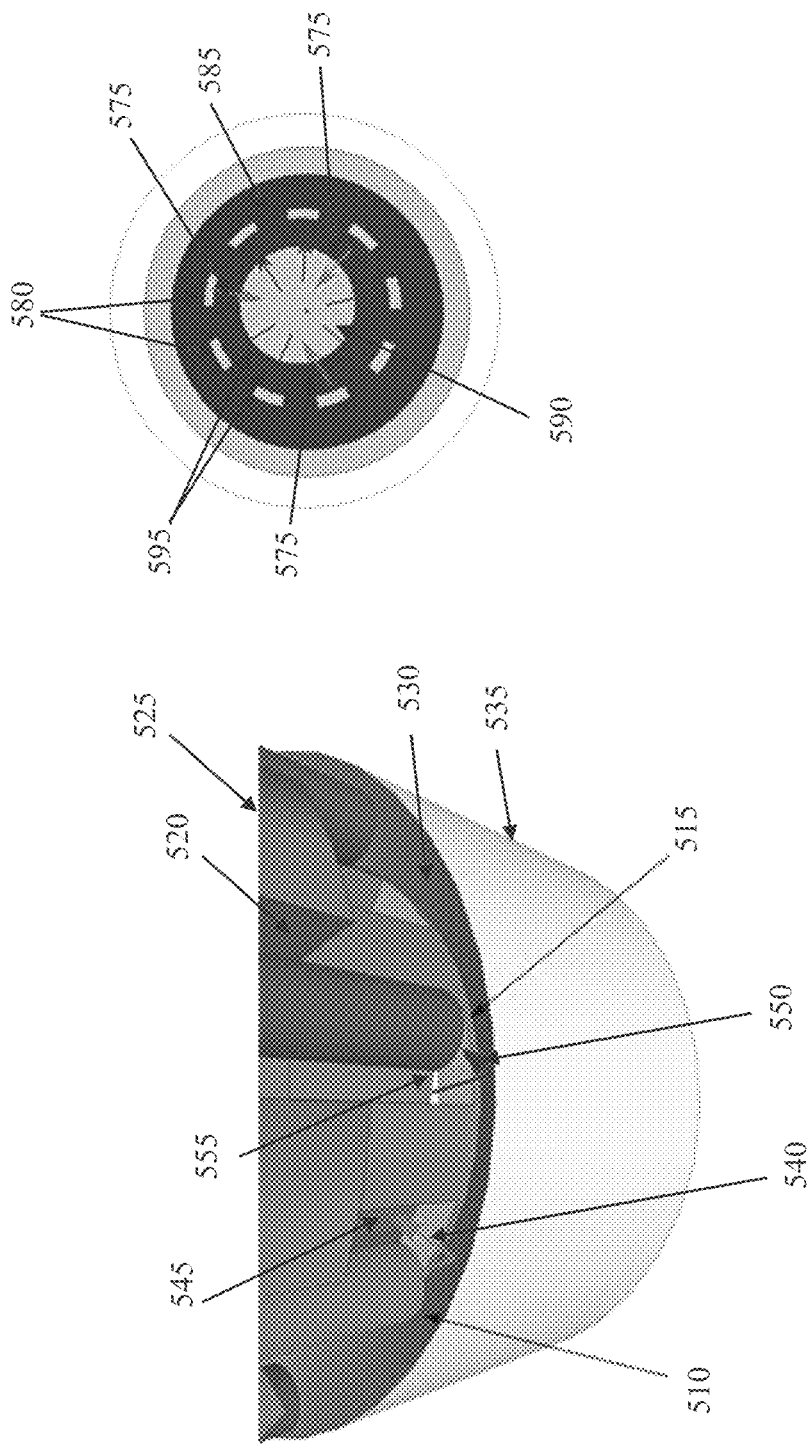
FIG. 5 illustrates a perspective cutaway view and bottom view of the suction tool tip/optical probe illustrated in FIG. 4.

FIG. 5 illustrates the relation between the signals from the optical fibers and the reflective surface of the ring proximal end. In this example, light signals refers to imaging techniques and excitation signals refers to spectroscopic techniques. In a transverse cutaway view, FIG. 5 left panel, the optical fibers 510, 515 extend through the channels 520 in the tip wall 525 to near the distal end of the tip. The reflective surface 530 of the ring 535 opposes the ends of the optical fibers 510, 515. Light or excitation signals 540 pass from an optical fiber 510 to the reflective surface 530, which reflects the light/excitation signal through the port 545 in the inner wall of the tip, toward the inner diameter of the tip. Thus the light/excitation signals 540 are directed by the ring 535 onto the tissue at the distal end of the tip. Reflected light or excitation signals 550 travel back through a port 555 in the inner wall of the tip and are reflected by the reflective surface 530 of the ring 535 onto collection optical fibers 515.

FIG. 5 right panel illustrates a bottom view of the tip and optical signals. Light/excitation signals 575 pass through ports 580 in the inside tip wall 585 onto the beveled surface 590 of the ring and reflective signals 595 are reflected from the beveled surface through ports 580 in the inside tip wall 585 to be collected by a collection optical fiber.

Figure 6:
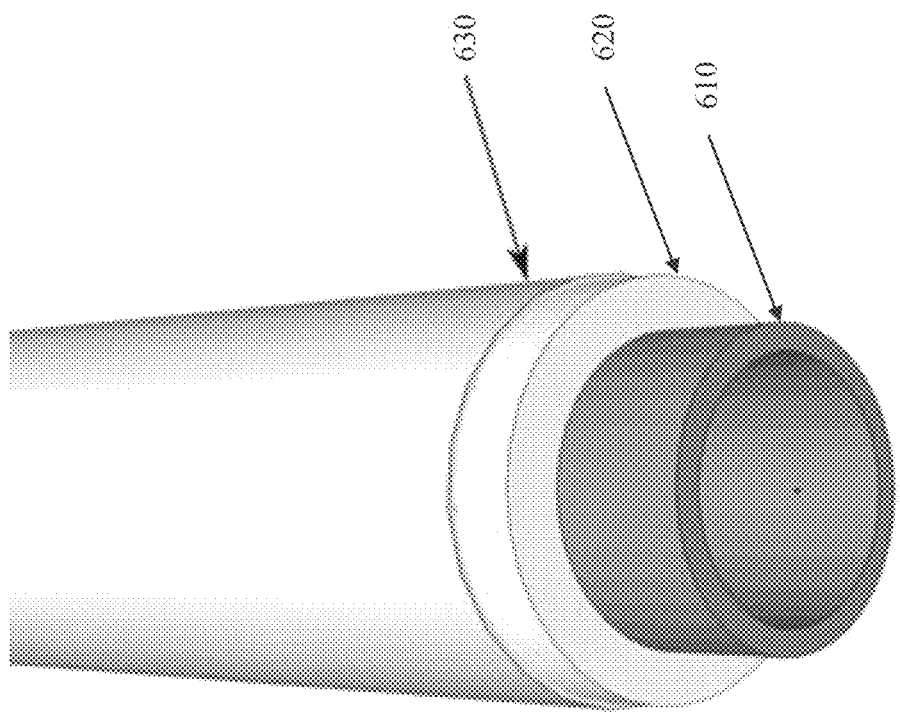
FIG. 6 illustrates a sealed suction tool tip/optical probe.

As illustrated in FIG. 6, the components of the suction/optical probe, including the tip wall 610 and ring 620 are sealed. The components may be epoxied and sealed with a thin sleeve 630, such as a thermal shrink tubing, to exclude fluids from entering during surgery and prevent tissue and fluids from lodging near the optical fibers and blocking optical signals.

Figure 7:
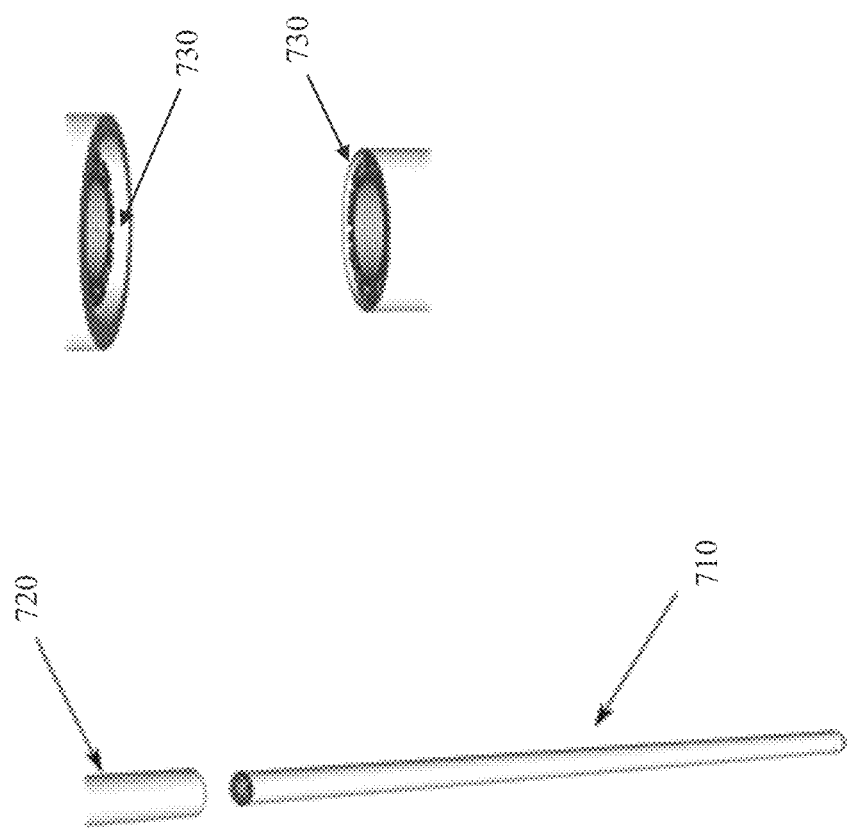
FIG. 7 illustrates a perspective view of an attachment of a suction tool tip/optical probe to a suction tool handle.

The suction tool tip is attached to an elongated tubular handle, having a centrally longitudinal passage, as illustrated in FIG. 7. The tip 710 is reversibly attached to the suction tool handle 720, thus allowing consumable tips to be used with a permanent suction handle. Examples of reversible attachment mechanisms for lockably attaching the tip 710 to the handle 720 are a snap mechanism or a threaded ring mechanism. The tip 710 and handle 720 are attached such that optical fibers in the tip are aligned with complementary optical fibers in the handle at the attachment point 730, for example using asymmetric tabs and complementary recesses.

Figure 8:
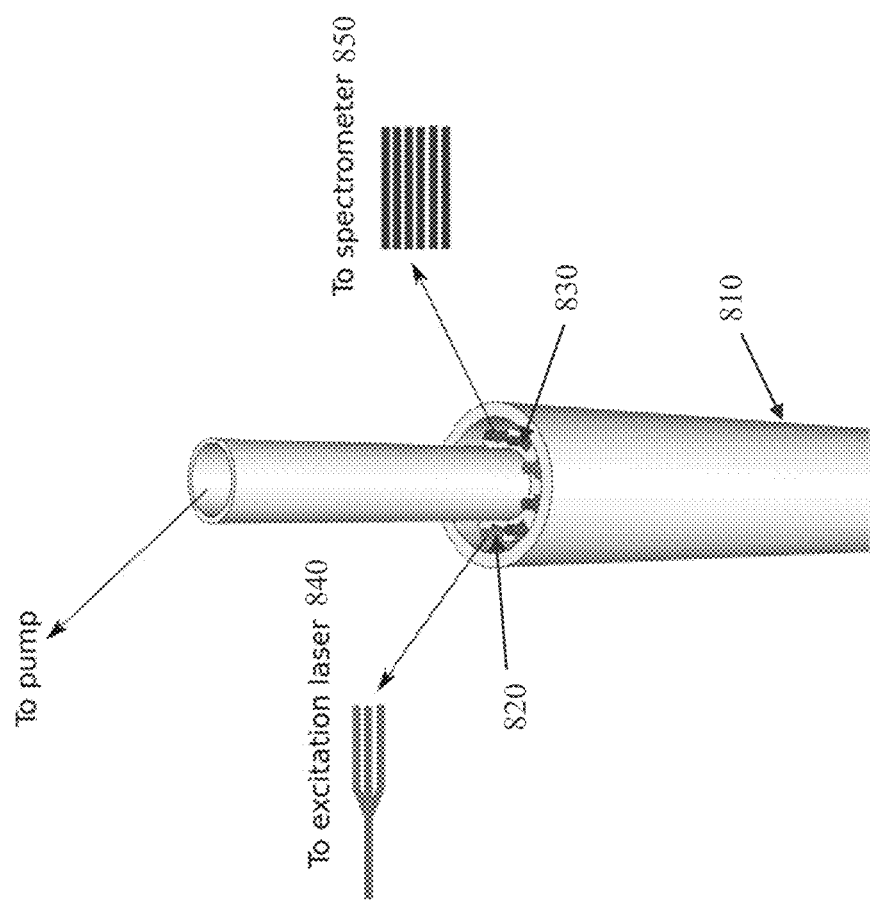
FIG. 8 illustrates a cutaway view of a suction tool handle combined with an optical probe.

As illustrated in FIG. 8, the suction tool handle 810 houses optical fibers 820, 830 for light/excitation signals and collection signals. The handle optical fibers 820, 830 are complementary to and align with the optical fibers in the suction tool tip. A hollow longitudinal passage in the handle connects to a pump or other vacuum source.

In an embodiment wherein the optical probe incorporates spectroscopic techniques, preferably such as Raman spectroscopy, time resolved and spectrally resolved fluorescence techniques, excitation optical fibers 820 from the handle are connected to an excitation light source 840, while collection optical fibers 830 are connected to a spectrometer or detector 850. Collection signals may be analyzed using a computer device and data from the signals may be presented on a computer display and correlated with images, including images obtained prior to the surgical procedure and images of the position of the suction tool based on tracking markers.

In an embodiment wherein the optical probe incorporates imaging techniques such as Optical Coherence Tomography, any one of the fibers in optical fibers 820 and 830 can be coupled to an OCT module instead of an excitation laser or a spectrometer. The OCT module will direct laser light to the tissue through an internal interferometer to the fiber 820 or 830. Light scattered from the laser light will be collected through the same fiber 820 or 830 back to the interferometer to generate light interference with an internal reflected light which is then directed to a detector for detection. Note that the detection of the scatter light for OCT could also be a spectrometer or a photodetector. A real time varying one dimensional (A-scan) can be obtained using this configuration. Further information on OCT system and methods can be found in PCT application PCT/IB2017/050226 entitled "SYSTEM AND METHOD FOR PROVIDING SURGICAL GUIDANCE BASED ON POLARIZATION-SENSITIVE OPTICAL COHERENCE TOMOGRAPHY" which is incorporated by reference herein.

Figure 9:
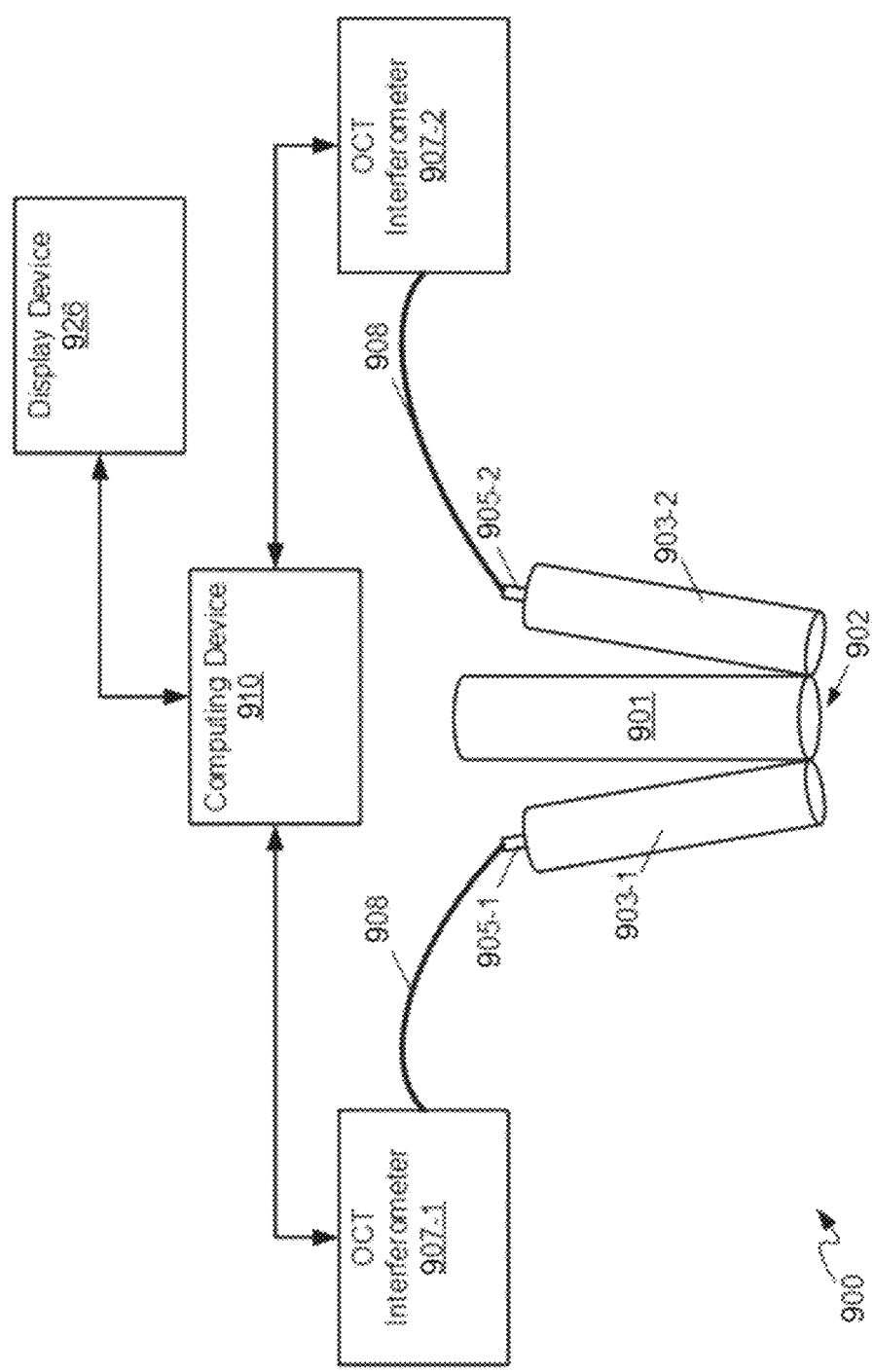
FIG. 9 illustrates an imaging probe of the device of FIG. 4.

In an alternate embodiment illustrated in FIG. 9, wherein the optical probe 903-1, 903-2 (hereafter collectively referred to as optical probe 903) aspect of the suction device 901 incorporates imaging techniques, such as optical coherence tomography (OCT), the optical fibers connect through an optical fiber 908 to an interferometer 907-1, 907-2 (hereafter collectively referred to as interferometer 907). Light, such as laser light, from the interferometer 907 passes through the optical fibers and is scanned across tissue by the optical probe 903, and the optical probe collects light scattered from the tissue. Hence, in this embodiment, the optical probe 903 comprises a scanning component including but not limited to a MEMS (microelectromechanical) and a photoacoustic scanner, and a focusing element including micro-lens, Gradient-Index (GRIN) lenses and ball lenses. The scanning component is configured to scan OCT light across a line and/or an area of tissue to obtain a two or three dimensional OCT image respectively.

Each OCT interferometer may comprise a light source, one or more optical couplers and/or beam splitters, and a reference arm that may comprise at least a reference mirror, and at least one detector. The light source may be directed to an optical coupler and/or beam splitter which splits the OCT light (e.g. laser light) into a reference arm and a sample arm. In the reference arm, the OCT light is directed to a mirror that sets a reference imaging distance from optical coupler and/or beam splitter. The OCT light then reflects back to the optical coupler and/or beam splitter. In the sample arm, the optical coupler and/or beam splitter may direct the OCT light to a respective optical probe which, in turn, directs the OCT light to tissue to generate light scattering from the tissue. The reflected light from tissue is received through the same OCT probe which directs the light back to the optical coupler in the OCT interferometer. The reflected light from tissue and the reference mirror then interferes and forms a fringe pattern which creates an A-scan OCT signal through Fourier transformation. As an OCT scan is performed, the OCT interferometer produces an OCT output, which is received by a computing device 910 and combined at a display device 926 in an OCT image.

The suction/optical probe may be used intraoperatively to provide guided insertion and use of a suction tool. The suction tool tip is attached to the handle, using a locking mechanism for reversibly attaching the tip and handle. The attachment mechanism also provides alignment of optical fibers embedded in the tip and handle. The handle is attached to a suction or vacuum pump to provide suction. The tip is guided through a tissue, while optical signals travel from a light source, through the optical fibers in the handle and corresponding optical fibers in the tip, and from the distal end of the optical fibers onto the reflective surface of the ring, which directs the optical signal forward and inward to the tissue ahead of the suction/optical tool. Optical signals from the tissue are collected back on the reflective surface of the ring, and onto the collection optical fibers in the tip, through the collection optical fibers in the handle, to a spectrometer or detector. The collection optical signals are read and analyzed to provide imaging or spectroscopy of the tissue in front of the probe as the probe is inserted toward the target tissue. Using the information from the optical signals to identify whether the measured tissue is the target tissue, the tissue may be suctioned, resected or ablated using the suction tool/optical probe.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:
1. A suction device for use in a medical procedure comprising:
  an elongated tip, having a hollow tubular body, an outer wall, a tip proximal end and a tip distal end;
  a plurality of optical fibers embedded in the outer wall of the tip body, extending from the tip proximal end to near the tip distal end and externally accessible at the tip proximal end and near the tip distal end;
  a concentric ring attached to the tip, having a first end and a second end, wherein the first end is attached to the tip distal end and the first end has an inner beveled reflective surface opposing the optical fibers near the tip distal end;
  an elongated tubular handle, having a central longitudinal passage, a handle proximal end and a handle distal end, the handle proximal end reversibly attached to a vacuum source and the handle distal end reversibly attached to the tip proximal end;
  a plurality of handle optical fibers embedded in the handle, extending from the handle proximal end to the handle distal end and wherein the optical fibers at the tip proximal end align with the handle optical fibers at the handle distal end;
  a light source connected to one or more of the handle optical fibers; and
  a spectrometer or a detector connected to one or more of the handle optical fibers.

2. The suction device as in claim 1, wherein the handle is attached to the tip by a snap mechanism or a threaded ring.

3. The suction device as in claim 1, wherein the inner beveled reflective surface angle is between 0 and 89 degrees.

4. The suction device as in claim 1, wherein the tip is bendable.

5. The suction device as in claim 1, wherein the optical fibers comprise one or more of: single mode fibers; multi-mode fibers; photonic crystal fibers; polarization-maintaining fibers; and metal coated fibers.

6. The suction device as in claim 1, wherein the concentric ring comprises a molded plastic piece that slides on the tip distal end.

7. The suction device as in claim 1, further comprising a thin sleeve sealing the tip and the ring.

8. The suction device as in claim 1, wherein the optical fibers comprise one or more excitation fibers and one or more detector fibers.

9. A suction device for use in a medical procedure comprising:
  an elongated tip, having a hollow tubular body with a tip inner wall, a tip outer wall, a tip proximal end and a tip distal end;
  one or more channels in the tip outer wall extending from the tip proximal end to near the tip distal end;
  optical fibers within the channels;
  optical ports through the tip inner wall and extending from the channels near the tip distal end, for optical signal passage;
  a concentric ring attached to the tip, having a first end and a second end, wherein the first end is attached to the tip distal end and the first end has an inner beveled reflective surface opposing the optical ports near the tip distal end;
  an elongated tubular handle, having a central longitudinal passage, a handle proximal end and a handle distal end, the handle proximal end reversibly attached to a vacuum source and the handle distal end reversibly attached to the tip proximal end;
  a plurality of handle optical fibers embedded in the handle, extending from the handle proximal end to the handle distal end and wherein the optical fibers at the tip proximal end align with the handle optical fibers at the handle distal end;

a light source connected to one or more of the handle optical fibers; and a spectrometer or a detector connected to one or more of the handle optical fibers.

10. The suction device as in claim 9, wherein the optical ports are sealed with an optically transparent resin.

11. The suction device as in claim 9, wherein the handle is attached to the tip by a snap mechanism or a threaded ring.

12. The suction device as in claim 9, wherein the inner beveled reflective surface angle is between 0 and 89 degrees.

13. The suction device as in claim 9, wherein the tip is bendable.

14. The suction device as in claim 9, wherein the optical fibers comprise one or more of: single mode fibers; multi-mode fibers; photonic crystal fibers;
polarization-maintaining fibers; and metal coated fibers.

15. The suction device as in claim 9, wherein the concentric ring comprises a molded plastic piece that slides on the tip distal end.

16. The suction device as in claim 9, further comprising a thin sleeve sealing the tip and the ring.

17. The suction device as in claim 9, wherein the optical fibers comprise one or more excitation fibers and one or more detector fibers.

18. A method for optically measuring tissue in a medical procedure, comprising:

suctioning a tissue using a suction device, the suction device comprising a tip with optical fibers in a tip outer wall and a concentric ring attached to the tip, the concentric ring having a first end and a second end, the first end having an inner beveled reflective surface opposing the optical fibers;

sending a first optical signal along the optical fibers in the tip outer wall through the suction device;

directing the first optical signal from the optical fibers onto a tissue using the inner beveled reflective surface;

directing a collected optical signal from the tissue onto the optical fibers using the inner beveled reflective surface;

measuring the collected optical signal in a spectrometer or a detector; and releasing or resecting the tissue through the suction device.

19. A method for optically measuring tissue prior to ablation in a medical procedure, comprising:

sending a first optical signal along one or more optical fibers through a suction device, the suction device comprising a tip with optical fibers in a tip outer wall and a concentric ring attached to the tip, the concentric ring having a first end and a second end, the first end having an inner beveled reflective surface opposing the optical fibers;

directing the first optical signal from the optical fibers in the tip outer wall onto a tissue using the inner beveled reflective surface;

directing a collected optical signal from the tissue onto the optical fibers using the inner beveled reflective surface;

measuring the collected optical signals in a spectrometer or a detector; and ablating the tissue using an ablation optical signal along the optical fibers.

* * * * *